US012799508B2

(12) United States Patent
Ahn et al.

(10) Patent No.: US 12,799,508 B2
(45) Date of Patent: Nov. 17, 2026

(54) *PICHIA CIFERRII* MUTANT STRAIN HAVING IMPROVED SPHINGOLIPID AND SPHINGOID BASE PRODUCTIVITY, AND PREPARATION METHOD THEREFOR

(71) Applicant: Croda Korea Ltd, Iksan-si (KR)

(72) Inventors: Jung Oh Ahn, Daejeon (KR); Chang Pyo Han, Daejeon (KR); Min Jeong Jang, Daejeon (KR); Hee Un Kwon, Daejeon (KR); Tae Hee Lee, Seongnam-si (KR); Ju Hee Lee, Hwaseong-si (KR); Hye Jin Kim, Anyang-si (KR)

(73) Assignee: Croda Korea Ltd, Iksan-si (KR)

( * ) Notice: Subject to any disclaimer, the term of this patent is extended or adjusted under 35 U.S.C. 154(b) by 617 days.

(21) Appl. No.: 18/003,025

(22) PCT Filed: Jun. 10, 2021

(86) PCT No.: PCT/KR2021/007298

§ 371 (c)(1),
(2) Date: Dec. 22, 2022

(87) PCT Pub. No.: WO2021/261816

PCT Pub. Date: Dec. 30, 2021

(65) Prior Publication Data

US 2023/0242951 A1 Aug. 3, 2023

(30) Foreign Application Priority Data

Jun. 23, 2020 (KR) ........................ 10-2020-0076795

(51) Int. Cl.

| | |
|---|---|
| ***C12N 1/16*** | (2026.01) |
| ***C12N 15/10*** | (2006.01) |
| ***C12P 13/02*** | (2006.01) |
| ***C12R 1/84*** | (2006.01) |

(52) U.S. Cl.

CPC ................ *C12P 13/02* (2013.01); *C12N 1/16* (2013.01); *C12N 15/102* (2013.01); *C12N 2500/30* (2013.01); *C12R 2001/84* (2021.05)

(58) Field of Classification Search

CPC .......... C12P 13/02; C12P 7/6436; C12N 1/16; C12N 15/102; C12N 2500/30; C12N 9/001; C12N 15/815; C12R 2001/84

See application file for complete search history.

(56) References Cited

U.S. PATENT DOCUMENTS

| | | | |
|---|---|---|---|
| 9,388,439 | B2 | 7/2016 | Schaffer et al. |
| 9,404,118 | B2 | 8/2016 | Kohler et al. |
| 2014/0199736 | A1 | 7/2014 | Kohler et al. |
| 2015/0353966 | A1 | 12/2015 | Beardslee et al. |
| 2016/0304916 | A1 | 10/2016 | Kohler et al. |
| 2018/0258434 | A1 | 9/2018 | Beardslee et al. |
| 2019/0144897 | A1 | 5/2019 | Zhu et al. |

FOREIGN PATENT DOCUMENTS

| | | | |
|---|---|---|---|
| JP | 2016-501041 | A | 1/2016 |
| JP | 2018-519843 | A | 7/2018 |
| KR | 10-0188857 | B1 | 6/1999 |
| KR | 10-0221357 | B1 | 10/1999 |
| KR | 10-2014-0063599 | A | 5/2014 |
| KR | 10-2056651 | B1 | 12/2019 |
| WO | 2007/131720 | A1 | 11/2007 |

OTHER PUBLICATIONS

Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Sadowski et al., Current Opinion in Structural Biology 19:357-362, 2009.*
Singh et al., Current Protein and Peptide Science 19(1):5-15, 2018.*
Zhou et al., Cell Mol Life Sci 63(19-20):2260-2290, 2006.*
Kozak, M., Gene 234:187-208, 1999.*
Schneider et al., GenBank accession No. XM_011279073, Feb. 6, 2015.*
Pfleger et al., Metabolic Engineering 29:1-11, 2015.*
Schneider et al., GenBank accession No. CCH40726, Sep. 13, 2012.*
Schneider et al., GenBank accession No. CCH41258, Sep. 13, 2012.*
Christoph Schorsch et al., "Knockout of the DNA ligase IV homolog gene in the sphingoid base producing yeast *Pichia ciferrii* significantly increases gene targeting efficiency", Curr Genet, 2009, vol. 55, pp. 381-389 (9 pages total).
Jessica Schneider et al., "Draft Genome Sequence of *Wickerhamomyces ciferrii* NRRL Y-1031 F-60-10", Eukaryotic Cell, Dec. 2012, vol. 11, No. 12, pp. 1582-1583 (2 pages total).
Christoph Schorsch et al., "High-level production of tetraacetyl phytosphingosine (TAPS) by combined genetic engineering of sphingoid base biosynthesis and L-serine availability in the non-conventional yeast *Pichia ciferrii*", Metabolic Engineering, 2012, vol. 14, pp. 172-184 (13 pages total).
Ai-Qun Yu et al., "Production of fatty acid-derived valuable chemicals in synthetic microbes", Frontiers in Bioengineering and Biotechnology, Dec. 2014, vol. 2, Article 78, pp. 1-12 (12 pages total).
Jung-Hoon Bae et al. "Integrative Transformation System for the Metabolic Engineering of the Sphingoid Base-Producing Yeast *Pichia ciferrii*", Applied and Environmental Microbiology, Feb. 2003, vol. 69, No. 2, pp. 812-819 (8 pages total).

(Continued)

*Primary Examiner* — Delia M Ramirez
(74) *Attorney, Agent, or Firm* — Buchanan Ingersoll & Rooney PC

(57) ABSTRACT

The present disclosure relates to a novel yeast mutant strain for producing a ceramide precursor, and a method for preparing the same, and more specifically, to a *Pichia ciferrii* mutant strain genetically engineered to overexpress sphingolipid metabolites prepared through the reconstruction of metabolic pathways for ceramide production in *Pichia ciferrii*, or a method for preparing the mutant strain.

10 Claims, 3 Drawing Sheets

Specification includes a Sequence Listing.

(56) References Cited

OTHER PUBLICATIONS

Jose Antonio Morales-Serna et al., "Recent Advances in the Synthesis of Sphingosine and Phytosphingosine, Molecules of Biological Significance", Current Organic Chemistry, 2010, vol. 14, No. 20, pp. 2483-2521 (39 pages total).
Lynferd J. Wickerham et al., "Formation of Extracellular Sphingolipides by Microorganisms", Journal of Bacteriology, 1960, vol. 80, pp. 484-491 (8 pages total).
Hanns G.. Maister et al., "Formation of Extracellular Sphingolipids by Microorganisms", Applied Microbiology, 1962, vol. 10, pp. 401-406 (6 pages total).
Thomas Pfeiffer et al., "Cooperation and Competition in the Evolution of ATP-Producing Pathways", Science, Apr. 20, 2001, vol. 292, pp. 504-507 (5 pages total).
Yechezkel Barenholz et al., "Identification of the enzymatic lesions responsible for the accumulation of acetylated sphingosine bases in the yeast *Hansenula ciferri*", Biochimica et Biophysica Acta, 1973, vol. 306, pp. 341-345 (5 pages total).
Cecile Fairhead et al., "New Vectors for Combinatorial Deletions in Yeast Chromosomes and for Gap-repair Cloning using Split-marker Recombination", Yeast, 1996, vol. 12, pp. 1439-1457 (20 pages total).
Jack T. Pronk, "Auxotrophic Yeast Strains in Fundamental and Applied Research", Applied and Environmental Microbiology, May 2002, vol. 68, No. 5, pp. 2095-2100 (6 pages total).
Heeseok Lee et al., "Development of a promising microbial platform for the production of dicarboxylic acids from biorenewable resources", Biotechnol Biofuels, 2018, vol. 11, Article 310, pp. 1-14 (14 pages total).
Lisa Klug et al., "Yeast lipid metabolism at a glance", FEMS Yeast Res, 2014, vol. 14, pp. 369-388 (20 pages total).
International Search Report dated Sep. 6, 2021 issued by the International Searching Authority in Application No. PCT/KR2021/007298.
Written Opinion dated Sep. 6, 2021 issued by the International Searching Authority in Application No. PCT/KR2021/007298.
Börgel et al., "Metabolic engineering of the non-conventional yeast Pichia ciferrii for production of rare sphingoid bases", Metabolic Engineering, (Jul. 1, 2012), vol. 14(4), pp. 412-426.
Ter Veld, et al., "Production of tetraacetyl phytosphingosine (TAPS) in Wickerhamomyces ciferrii is catalyzed by acetyltransferases Sli1p and Atf2p", Applied Microbiology and Biotechnology, (Jan. 15, 2013), vol. 97(19), pp. 8537-8546.
The Extended European Search Report issued May 29, 2024 by the European Patent Office in corresponding European Application No. 21828118.6. (9 pages).
Wolff, et al., "Combined application of targeted and untargeted proteomics identifies distinct metabolic alterations in the tetraacetylphytosphingosine (TAPS) producing yeast Wickerhamomyces ciferrii", Journal of Proteomics, (Apr. 1, 2013), 82, pp. 274-287.
Yoo et al., "Wickerhamomyces ciferrii auxotroph and expression vector for improved production of tetraacetyl phytosphingosine", Biotechnology and Bioprocess Engineering, (Oct. 1, 2023), vol. 28(5), pp. 804-812.

* cited by examiner

*PICHIA CIFERRII* MUTANT STRAIN HAVING IMPROVED SPHINGOLIPID AND SPHINGOID BASE PRODUCTIVITY, AND PREPARATION METHOD THEREFOR

CROSS REFERENCE TO RELATED APPLICATIONS

This application is a National Stage of International Application No. PCT/KR2021/007298 filed Oct. 6, 2021. Further, this application claims the benefit of Korean Patent Application No. 10-2020-0076795 filed on Jun. 23, 2020, with the Korean Intellectual Property Office, the disclosure of which is herein incorporated by reference in its entirety.

INCORPORATION BY REFERENCE OF SEQUENCE LISTING

The content of the electronically submitted sequence listing, file name: Q282263_Sequence_Listing_As_Filed.txt; size: 31,443 bytes; and date of creation: Dec. 22, 2022, filed herewith, is incorporated herein by reference in its entirety.

TECHNICAL FIELD

The present disclosure relates to a *Pichia ciferrii* mutant strain with improved productivity of sphingolipids and sphingoid bases by regulating fatty acid metabolism, and a method for preparing the same.

BACKGROUND ART

Sphingolipid refers to a group of lipids derived from sphingoid bases, and is a common name for ceramides or ceramide derivatives that have sphingosine, phytosphingosine, and sphinganine as their basic skeletons in the human body. Sphingolipid is naturally present in large amounts in the cell membranes of animals, plants and microorganisms, and is involved in various cell signaling such as cell differentiation, cell growth and cell death.

It is known that ceramides have both hydrophilic and lipophilic groups to prevent evaporation of moisture from the skin, as well as to act as a defense substance with permeability to the stratum corneum of human skin and homeostasis against microorganisms. Recently, ceramides have been used as useful substances in cosmetics.

Tetraacetyl phytosphingosine (TAPS), which is valuable as a precursor of ceramide, is a substance produced in a completely acetylated state by N, O-acetylation of phytosphingosine in sphingoid bases, and is easily converted back to phytosphingosine through a deacetylation reaction. The chemical structure of the converted phytosphingosine has the same D-erythro isomer structure as the ceramide structure of human skin, and thus, it may be used as a raw material for producing ceramide friendly to human skin.

TAPS may be chemically synthesized (Current Organic Chemistry, 2010. 14(20) 2483-2521), but the process is complicated and the production cost is high. Therefore, as a method for replacing it from an economic point of view, production through biological methods is attracting attention. It was found that among them, *Pichia ciferrii* produced a large amount of sphingoid bases and sphingolipids including TAPS (Journal of bacteriology, 1960, 80(4) 484-491), and afterwards, a brief process for the biosynthesis of TAPS was known through genome sequencing (Eukaryotic cell, 2012, 11(12) 1582).

Wild-type *Pichia ciferrii* was known to produce 233 mg/L of TAPS at a yield of 5 mg (TAPS)/g (glucose) in an experiment conducted for research purposes (Applied Microbiology, 1962, 10(5) 401). In addition, the newly isolated *Pichia ciferrii* DSCC 7-25 showed a TAPS production yield of 1,065 mg/L through the method of adjusting culture conditions and separating and purifying sphingolipids (Korean Patent No. 10-0221357, Korean Patent No. 10-0188857). However, this is nothing more than a production yield improvement at the laboratory level, and does not reach the level of mass production for industrial use.

Therefore, the present disclosure is intended to provide a *Pichia ciferrii* mutant strain with increased production yield of TAPS to enable industrial utilization and a method for producing the same.

PRIOR ART REFERENCES

Patent Documents

Korean Patent No. 10-0221357
Korean Patent No. 10-0188857
Korean Patent No. 10-2056651

Non-Patent Documents

Current Organic Chemistry, 2010. 14(20) 2483-2521
Journal of bacteriology, 1960, 80(4) 484-491
Eukaryotic cell, 2012, 11(12) 1582
Applied Microbiology, 1962, 10(5) 401
Science 2001, 292(5516) 504
Biochimica et Biophysica Acta (BBA)—Lipids and Lipid Metabolism, 1973. 306(2) 341-345

DISCLOSURE

Technical Problem

It is an object of the present disclosure to provide a genetically engineered *Pichia ciferrii* mutant strain with increased productivity of sphingolipids and sphingoid bases and a method for preparing the same.

Additionally, it is another object of the present disclosure to provide a method for producing TAPS, which is a ceramide precursor, using the genetically engineered *Pichia ciferrii* mutant strain.

Technical Solution

In order to achieve the above objects, the present disclosure provides a genetically engineered *Pichia ciferrii* mutant strain.

According to an embodiment of the present disclosure, there is provided a *Pichia ciferrii* mutant strain in which the expression of a gene related to β-oxidation of palmitoyl-CoA is suppressed to increase palmitoyl-CoA accumulation in the cell.

According to an embodiment of the present disclosure, there is provided a *Pichia ciferrii* mutant strain in which the PcPOX3 gene, a gene related to p-oxidation of palmitoyl-CoA, is deleted to suppress its expression.

According to an embodiment of the present disclosure, there is provided a *Pichia ciferrii* mutant strain in which the expression of the PcLCB4 gene, which is a gene involved in phosphorylation of sphingoid bases, is further suppressed in the PcPOX3 gene-deleted *Pichia ciferrii* cell.

According to an embodiment of the present disclosure, there are provided a culture method and a production method of tetraacetyl phytosphingosine (TAPS), for increasing the production of TAPS, which is a precursor of ceramide, in the cell.

According to an embodiment of the present disclosure, there is provided a method for producing TAPS, which is a precursor of ceramide, in the *Pichia ciferrii* mutant strain.

Advantageous Effects

The *Pichia ciferrii* mutant strain provided by the present disclosure provides a genetically engineered *Pichia ciferrii* strain with increased productivity of sphingolipids and sphingoid bases compared to its wild type. In addition, the present disclosure provides an environmentally friendly production method capable of producing sphingolipids and sphingoid bases through biological methods.

BEST MODE

Figure 1:
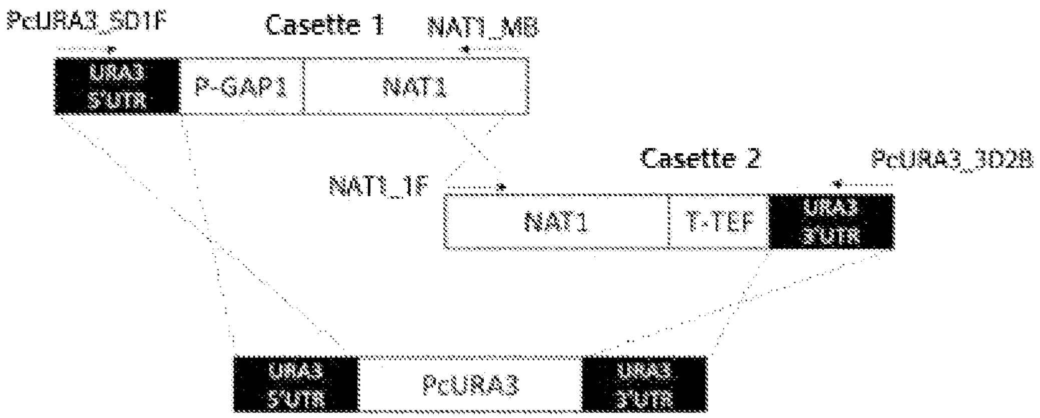
FIG. 1 shows the construction diagram of the auxotrophic PcURA3 gene deletion cassette vector.

Hereinafter, the present disclosure will be described in more detail in order to facilitate understanding of the present disclosure.

*Pichia ciferrii* is the only yeast with the ability to produce and secrete a large amount of fully acetylated sphingolipids, which cannot be found in other yeasts (Journal of bacteriology, 1960, 80(4) 484-491), and the exact origin of evolution to this phenotype has not yet been elucidated, but it is assumed that it evolved through competition to secure a carbon energy source in amino acid mass-producing yeasts or Crabtree-positive strains (Science 2001, 292(5516) 504).

*Pichia ciferrii* is an unconventional yeast strain, which was formerly named *Hansenula ciferrii* or *Pichia ciferrii*, but now reclassified to the genus Wickerhamomyces. However, in the present disclosure, in order to prevent confusion with the existing name, it was specified as *Pichia ciferrii* as per the existing name. The main feature of *Pichia ciferrii* is that it is the only yeast with the ability to produce and secrete a large amount of fully acetylated sphingoids, which cannot be found in other yeasts, and may produce and secrete TAPS, which is valuable as a precursor for cosmetic ceramides as described above.

The first step in the biosynthetic process of sphingolipids is the step of condensing serine and palmitoyl-CoA by serine palmitoyl transferase (3-ketosphinganine synthase) to form 3-ketosphinganine having 18 carbon atoms, and this step determines the rate of sphingolipid biosynthesis (Biochimica et Biophysica Acta (BBA)—Lipids and Lipid Metabolism, 1973. 306(2) 341-345).

There is a metabolic process in which palmitoyl-CoA, which is a raw material for TAPS biosynthesis together with serine (L-serine), is decomposed into acetyl-CoA by the 8-Oxidation process. Blocking this metabolic process may enhance the conversion of palmitic acid to palmitoyl-CoA, thereby inducing palmitoyl-CoA accumulation and increasing TAPS production.

The gene related to the enzyme that catalyzes the reaction of converting palmitoyl-CoA to trans-Δ2-enoyl-CoA in the 8-Oxidation process is known to be the PDX gene, and similar genes named PcPOX3 and PcPOX4 in *Pichia ciferrii* are also known. The accumulation rate of palmitoyl-CoA may be increased by suppressing the expression of the corresponding genes.

In addition, in fatty acid metabolism, PcLCB4 (sphinganine kinase LCB4) is an enzyme having a kinase activity that phosphorylates sphinganine and phytosphingosine, it is known that deletion of the PcLCB4 gene suppresses metabolism toward sphingosine, thereby increasing TAPS production (Korean Patent No. 10-2056651).

The present disclosure relates to a *Pichia ciferrii* mutant strain in which the expression of the PcPOX3 gene (SEQ ID NO: 28) or the PcPOX3 (SEQ ID NO: 28) and PcLCB4 (SEQ ID NO: 29) genes is suppressed, and a method for suppressing the expression of the genes includes partial or total deletion of each gene, insertion of foreign DNA, replacement of a part of a gene with a foreign gene, RNA interference, induction of gene mutation, or a combination thereof, specifically, is by partial or total deletion of each gene, and more specifically, is by total deletion of each gene.

In the present disclosure, the accumulation rate of palmitoyl-CoA may be increased by constructing a deletion cassette targeting the corresponding genes, and in the present disclosure, the PcPOX3 gene-deleted *Pichia ciferrii* mutant strain and the PcPOX3 and PcLCB4 genes-co-deleted *Pichia ciferrii* mutant strain were prepared and increased TAPS production was confirmed.

It is understood that the reduction in enzyme activity is compared to a wild-type *Pichia ciferrii* strain.

The "wild-type" of a cell in the context of the present disclosure preferably refers to the parental strain from which the cell according to the present disclosure is developed through modification of elements affecting the activity of an enzyme encoded by a specified nucleic acid sequence (for example, a gene comprising a specified nucleic acid sequence encoding the corresponding enzyme, or a promoter present in the corresponding gene and functionally linked to the specified nucleic acid sequence).

The "reduction in enzyme activity" compared to wild-type preferably refers to an activity that is reduced by at least 50%, particularly preferably by at least 90%, further preferably by at least 99.9%, further more preferably by at least 99.99%, and most preferably by at least 99.999% compared to the wild-type activity.

The reduction in specific activity of the cells according to the present disclosure compared to its wild-type may be measured by, but not limited to, a method for measuring activity by using cells grown under the same conditions, such as equivalent cell numbers/concentrations, for example, media, gas treatment, and agitation, if possible.

The yeast mutant strain of the present disclosure is a mutant strain in which a sphingolipid metabolic pathway is redesigned using a wild-type *Pichia ciferrii* strain as a parent strain, and preferably, the *Pichia ciferrii* DSCC 7-25 (Accession No. KFCC-10937) strain disclosed in the Examples of Korean Patent No. 10-0188857 may be used, or any strain having the sphingolipid metabolic pathway may be used as a parent strain without any limitation to the strain.

In an embodiment of the present disclosure, TAPS production (TAPS-specific yield) in the mutant strain through the above method was about 1.7-fold in the PcPOX3 gene-deleted mutant strain, and 2-fold or more in the PcPOX3 and PcLCB4 genes-co-deleted mutant strain.

An embodiment of the present disclosure provides a method for increasing TAPS production by adding fatty acid methyl esters to the culture medium of the mutant strain to artificially accumulate fatty acids in cells. As a result, the TAPS-specific yield increased to about 100% in the PcPOX3 gene-deleted mutant strain.

With respect to the above-mentioned sequences, "nucleotide identity" may be measured with the aid of known methods. In general, special computer programs are used with algorithms that take into account special requirements.

It is another object of the present disclosure to provide the mutant strain according to the present disclosure that produces sphingoid bases and sphingolipids.

The term "sphingoid base" in the context of the present disclosure refers to one selected from phytosphingosine, sphingosine, sphingadienine, 6-hydroxysphingosine and sphinganine (dihydrosphingosine), and their acetylated forms, such as, for example, tetraacetylphytosphingosine, triacetylphytosphingosine, diacetylphytosphingosine, O-acetylphytosphingosine, triacetylsphinganine, diacetylsphinganine, O-acetylsphinganine, triacetylsphingosine, diacetylsphingosine, O-acetylsphingosine, tetraacetyl-6-hydroxysphingosine, triacetyl-6-hydroxysphingosine, diacetyl-6-hydroxysphingosine, O-acetyl-6-hydroxysphingadienine, triacetylsphingadienine, diacetylsphingadienine, and O-acetylsphingadienine.

The term "sphingolipid" in the context of the present disclosure is understood to refer to a compound comprising a sphingoid base covalently bonded to a fatty acid via an amide bond. The fatty acid may be saturated or mono- or polyunsaturated. The fatty acid side chains may vary in length. The fatty acid side chains may also contain functional groups such as hydroxyl groups. The sphingolipids include, for example, phytoceramides, ceramides and dihydroceramides, and the more complex glucosylceramides (cerebrosides) and inositol phosphorylceramides, mannosylinositol phosphorylceramides and mannosyldiinositol phosphorylceramides. In this case, the sphingolipids also include sphingoid bases bonded to an acetyl radical via an amide bond, such as, for example, N-acetylphytosphingosine, N-acetylsphinganine, N-acetylsphingosine and N-acetyl-6-hydroxysphingosine. These compounds are also known by the term short-chain ceramides.

The use of the mutant strain according to the present disclosure is advantageous for producing sphingolipids and sphingoid bases selected from the group consisting of phytosphingosine, sphingosine, sphingadienine, 6-hydroxysphingosine, sphinganine (dihydrosphingosine), tetraacetylphytosphingosine (TAPS), triacetylphytosphingosine, diacetylphytosphingosine, O-acetylphytosphingosine, N-acetylphytosphingosine, triacetylsphinganine (TriASa), diacetylsphinganine, O-acetylsphinganine, N-acetylsphinganine, triacetylsphingosine (TriASo), diacetylsphingosine, O-acetylsphingosine, N-acetylsphingosine, tetraacetyl hydroxysphingosine, triacetyl-6-hydroxysphingosine, diacetyl-6-hydroxysphingosine, O-acetyl-6-hydroxysphingosine, N-acetyl-6-hydroxysphingosine, triacetylsphingadienine, diacetylsphingadienine, and O-acetylsphingadienine. The use of the mutant strain according to the present disclosure for producing tetraacetylphytosphingosine (TAPS) is preferred.

It is another object of the present disclosure to provide a method for producing the above-described mutant strain according to the present disclosure. The method comprises the steps of:

a) providing a *Pichia ciferrii* strain, and
b) modifying at least one gene involved in β-oxidation by insertion of foreign DNA or DNA encoding a selectable marker gene into the gene, deletion of at least a portion of a gene, point mutation in a gene sequence, exposure of a gene to the effects of RNA interference, and partial replacement of a gene by foreign DNA or foreign DNA in a promoter region.

The *Pichia ciferrii* mutant strain according to the present disclosure may be used to prepare sphingoid bases and sphingolipids, and is preferably suitable for, but is not limited to, improving the production yield of tetraacetylphytosphingosine (TAPS).

Hereinafter, a method for producing sphingoid bases and sphingolipids using the *Pichia ciferrii* mutant strain according to the present disclosure will be described in detail, comprising the steps of:

a) contacting the genetically modified mutant strain according to an embodiment with a medium containing a carbon source;
b) culturing the strain under conditions that allow the strain to produce sphingoid bases and sphingolipids from the carbon source; and
c) optionally, isolating the resulting sphingoids base and sphingolipids.

Hereinafter, an additional method for producing sphingoid bases and sphingolipids using the *Pichia ciferrii* mutant strain according to the present disclosure will be described in detail, comprising the steps of:

a) contacting the genetically modified mutant strain according to an embodiment with a medium containing a carbon source and fatty acid methyl ester (FAME);
b) culturing the mutant strain under conditions that allow the mutant strain to produce sphingoid bases and sphingolipids from the carbon source; and
c) optionally, isolating the resulting sphingoids base and sphingolipids.

The carbon source that may be used in the step of culturing the cell includes carbohydrates, such as, for example, glucose, fructose, glycerol, sucrose, maltose, molasses, or other alcohols, such as, for example, ethanol, and organic acids, such as, for example, acetate. The nitrogen source that may be used includes, for example, ammonia, ammonium sulfate, ammonium nitrate, ammonium chloride, organic nitrogen compounds (for example, yeast extract, malt extract, peptone, corn steep liquor). Inorganic compounds, such as, for example, phosphates, magnesium salts, potassium salts, zinc salts, iron salts and the like may also be used.

Suitable culture conditions for the *Pichia ciferrii* strain of the present disclosure are known to those skilled in the art, for example, from International Publication No. WO 2007/131720 or Korean Patent No. 10-0221357.

Hereinafter, the present disclosure will be described in detail by way of examples.

However, the following examples are only for illustrating the present disclosure, and the content of the present disclosure is not limited to the following examples. The scope of use of the disclosure follows the entire detailed description and claims.

[Best Mode]

EXAMPLE

<Example 1> Construction of an Auxotrophic Gene Deletion Cassette

Unless otherwise specified, the subsequent construction of the cassette was constructed by *E. coli* plasmid cloning.

Gene deletion was performed by replacing DNA by classical homologous recombination and double cassette utilization (Yeast, 1996. 12(14): 1439-1457).

The present inventors first discovered and deleted the auxotrophic gene PcURA3 for efficient utilization of the marker gene, and then used it as a marker for deletion of the PcPOX3 and PcLCB4 genes (Example 2).

Specifically, a PcURA3 deletion cassette was constructed using the plasmid pGEM-T-easy (Promega) vector as a transfer vector. The pGEM-T-easy vector was cleaved using restriction enzymes SpeI and SacI, and the resulting 2.97 kb DNA fragment was used as a backbone for subsequent cloning.

The 600 bp sequence at the 5'-end of the GAPDH gene (SEQ ID NO: 1) isolated from the genome of wild-type *Pichia ciferrii* cells and the DNA-synthesized antibiotic nourseothricin resistance gene PcNAT1 (SEQ ID NO: 2) were amplified by PCR amplification.

The 5'-end (P-GAP1) of the PcGAPDH gene (SEQ ID NO: 1) was cleaved using restriction enzymes SpeI and NdeI, and the two DNA fragments of the PcNAT1 gene (SEQ ID NO: 2) cleaved using SacI and NdeI were ligated with the previously cleaved pGEM-T-easy vector fragment through T4 DNA ligase enzyme (TAKARA) treatment.

The GAPDH ends ligated on the vector were cleaved using restriction enzymes SpeI and EcoRI, and the resulting 4.147 kb DNA fragment was used as a backbone for subsequent cloning.

The 150 bp sequence T-PcTEF at the 3'-end of the PcTEF1 gene isolated from the genome of wild-type *Pichia ciferrii* cells was amplified by PCR amplification (SEQ ID NO: 27).

The T-PcTEF was cleaved using restriction enzymes SpeI and EcoRI, and ligated with the GAPDH end of the previously cleaved pGEM-T-easy vector through T4 DNA ligase enzyme (TAKARA) treatment.

The GAPDH end (FIG. 1, P-GAP1) ligated on the vector, 1335 bp of DNA of PcNAT1 gene and PcTEF end (FIG. 1, T-PcTEF), 1171 bp of the 5'-end and 548 bp of 3'-end of PcURA3 gene (SEQ ID NO: 3) isolated from the genome of wild-type *Pichia ciferrii* cells were amplified by PCR. At this time, the PcGAPDH end and the 5'-end of the PcURA3 gene, and the PcTEF gene end and the 3'-end of the PcURA3 gene were overlapped by 22 bp and 25 bp.

Cassette 1 in FIG. 1 was amplified by PCR using the primer NAT1_MB (cacctgaatcaggatattcttctaatacctgg; SEQ ID NO: 9) located at 324 bp from the initiation codon of the PcNAT1 gene and the primer PcURA3_5D1F (tgagaaacgtggcaatggatcattg; SEQ ID NO: 10) located at 1171 bp of the 5'-end of the PcURA3 gene (SEQ ID NO: 3).

Cassette 2 in FIG. 1 was amplified by PCR using the primer NAT1_1F (atgggtaaggaaaagactcacgttt; SEQ ID NO: 11) located at the initiation codon of the PcNAT1 gene and the primer PcURA3_3D2B (ttgtcactcttgaatggcatctactg; SEQ ID NO: 12) located at 548 bp of the 3'-end of the PcURA3 gene.

All primers described were marked in the 5' to 3' direction.

The PcURA3 gene (SEQ ID NO: 3) was deleted by transforming the deletion cassette (SEQ ID NO: 4) prepared by the method of Example 1 into a *Pichia ciferrii* strain, and the inserted cassette was confirmed through PCR and DNA sequencing (Figure

<Example 2> Construction of Gene Deletion Cassettes Related to Fatty Acid and Sphingolipid Metabolism The principle of construction of the basic cassette vector was the same as that of the auxotrophic gene deletion cassette.

In this example, the target gene to be constructed by a deletion cassette was PcPOX3, PcLCB4, or both PcPOX3 and PcLCB4. The deletion cassette was constructed using the plasmid pGEM-T-easy (Promega) as a transfer vector. The pGEM-T-easy (Promega) vector was cleaved using restriction enzymes NotI and SpeI, and the resulting 3.73 kb DNA fragment was used as a backbone for subsequent cloning.

Using the genome of wild-type *Pichia ciferrii* as a template, the ORF of the PcURA3 gene from 359 bp of the 5'-end to 387 bp of the 3'-end were amplified by PCR so as to overlap 30 bp with the SpeI-cleaved section of the pGEM-T-easy vector fragment described above.

Using the genome of wild-type *Pichia ciferrii* as a template, the 387 bp of the 3'-end of the PcURA3 gene was amplified by PCR so that the 5'-end overlapped 30 bp with the NotI-cleaved section of the previously described pGEM-T-easy vector fragment and the 3'-end overlapped 30 bp from 329 bp to 359 bp of the 5'-end of the URA3 gene.

The two DNA fragments previously amplified by PCR and the cleaved pGEM-T-easy vector fragment were made to have repetitive sequences at both ends of the PcURA3 gene through infusion cloning (TAKARA).

The 5'-end site and 3'-end site (Table 1) of the target gene to be deleted were amplified by PCR, respectively, and at this time, the 5'-end of the primer was extended to overlap 30-35 bp with the repetitive sequences of the marker gene to be fused (Table 1).

TABLE 1

List of corresponding primer sequences of genes to be deleted

| Gene name | Corresponding primer sequences of the target gene to be deleted | | | | | |
|---|---|---|---|---|---|---|
| | N1 | N2 | N3 | N4 | N5 | N6 |
| PcPOX 3 | gatgcatgc tcgagcAGT ATCAAATCA ATTACTTAT ACACTTATG ACTTTTATG (SEQ ID NO: 15) | AGTATCAAA TCAATTACT TATACACTT ATGACTTTT ATG (SEQ ID NO: 16) | TATATTGTT GACCgcATA ACCAGCTAA TTTCACAAT TTTTTTGAA AGCT (SEQ ID NO: 17) | cactggcgg ccgttaTTT CCATTACAT CAGAAAACA TTTCACAAT (SEQ ID NO: 18) | ccgagctcg gatccaATA TTTCCTTAA TATCCTTCT AACTTCTTC TTCA (SEQ ID NO: 19) | ATATTTCCT TAATATCCT TCTAACTTC TTCTTCA (SEQ ID NO: 20) |
| PcLCB 4 | gatgcatgc tcgagcAAA CTTATTCTC TTGTTTGGA | AAACTTATT CTCTTGTTT GGAACAC (SEQ ID | TATATTGTT GACCgcTTC AAATCTTGA AGGACCTAA | cactggcgg ccgttaCGT ATGGCACCA ACTTTATTA | ccgagctcg gatccaGCA ATTCTTGTT AAAGCAGCT | GCAATTCTT GTTAAAGCA GCTC (SEQ ID |

TABLE 1-continued

List of corresponding primer sequences of genes to be deleted

| Gene name | N1 | N2 | N3 | N4 | N5 | N6 |
|---|---|---|---|---|---|---|
| | ACAC (SEQ ID NO: 21) | NO: 22) | CC (SEQ ID NO: 23) | TC (SEQ ID NO: 24) | C (SEQ ID NO: 25) | NO: 26) |

The previously constructed vector was ligated with the DNA fragment cleaved using restriction enzyme NotI and the 5'-end amplified by PCR using primers N1 and N3 of the target gene to be deleted (FIG. 1), through infusion cloning (TAKARA).

The previously constructed vector was ligated with the DNA fragment cleaved using restriction enzyme SpeI and the 3'-end amplified by PCR using primers N4 and N5 of the target gene to be deleted, through infusion cloning (TAKARA).

Figure 2:
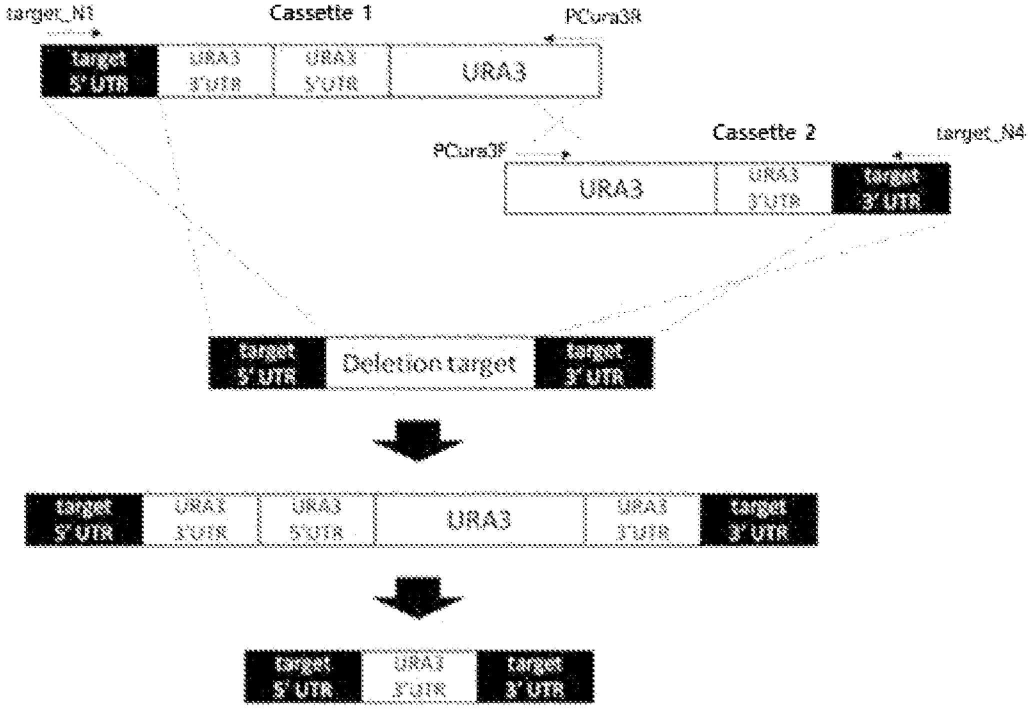
FIG. 2 shows the principle of construction and continuous deletion of a deletion cassette vector related to fatty acid metabolism.

Cassette 1 in FIG. 2 was amplified by PCR using the primer PcURA3R (GCTCTGTAACGTTCACCTTC; SEQ ID NO: 13) located inside 43 bp from the stop codon of the PcURA3 gene and the reverse primer (N2) of the target terminal site to be deleted inserted at the 5'-end of the marker gene.

Cassette 2 in FIG. 2 was amplified by PCR using the primer PcURA3F (ATTAGGTCCATATATCTGTCTTGTC; SEQ ID NO: 14) linked inside 150 bp gene from the initiation codon of the PcURA3 gene and the reverse primer (N6) of the target terminal site to be deleted inserted at the 3'-end of the marker gene.

All primers described were marked in the 5' to 3' direction.

Through this method, a specific gene deletion cassette having a PcPOX3 sequence (SEQ ID NO: 5, SEQ ID NO: 6) or a PcLCB4 sequence (SEQ ID NO: 7, SEQ ID NO: 8) was constructed.

The target gene was deleted by transforming the gene deletion cassette (SEQ ID NOs: 5 to 8) prepared by the method of Example 2 into a *Pichia ciferrii* strain, and the inserted cassette was confirmed through PCR and DNA sequencing.

For continuous gene deletion, *Pichia ciferrii* cells in which the marker gene was culled through recombination of repetitive sequences inserted at the 5'- and 3'-ends of the marker gene were constructed by addition of 5'-fluoroorotic acid and then confirmed by PCR.

<Example 3> Selection of Transformants

The constructed cassette was subjected to heat shock at a temperature of 37° C. for 15 minutes, and transformed into the parent strain DSCC 7-25 and strains derived therefrom, and it was confirmed by PCR amplification whether or not the target gene was expressed, and a desired transformant was selected.

<Example 4> TAPS Production of Transformants

Each of PcURA3 gene-deleted mutant strain in *Pichia ciferrii* DSCC 7-25 (Accession No. KFCC-1093) strain (BD 02), PcLCB4 gene-deleted mutant strain in the strain BD 02 (KD 02), PcPOX3 gene-deleted mutant strain in the strain BD 02 (KD 04), and PcLCB4 and PcPOX3 genes-co-deleted mutant strain in the strain BD 02 (KD 08) (Table 2) was inoculated into 50 ml of YGM optimal medium (glycerol 100 g/l, yeast extract 2 g/l, $KNO_3$ 3 g/l, $(NH_4)_2SO_4$ 0.5 g/l, $MgSO_4 \cdot 7H_2O$ 0.3 g/l, NaCl 0.5 g/l, CSL (corn steep liquor) 3 g/l, and LS-300 (anti-forming agent) 1 g/l) and cultured at 25° C. for 5 days at 220 rpm, and then, 4 volumes of methanol were added thereto and reacted at room temperature for 1 hour, and then, the centrifuged supernatant was analyzed for TAPS.

TAPS was analyzed by HPLC using UV 200 nm. An 84.5:18.45:0.05 mixture of methanol, water and TFA (trifluoroacetic acid) was used as a solvent.

TABLE 2

Characteristics of each mutant strain

| Strain name | Characteristics |
|---|---|
| BD 02 | Deletion of the PcURA3 gene in *Pichia ciferrii* DSCC 7-25 (Accession No. KFCC-10937) |
| KD 02 | Deletion of the PcLCB4 gene in strain BD 02 |
| KD 04 | Deletion of the PcPOX3 gene in strain BD 02 |
| KD 08 | Co-deletion of the PcPOX3 and PcLCB4 genes in strain BD 02 |

Figure 3:
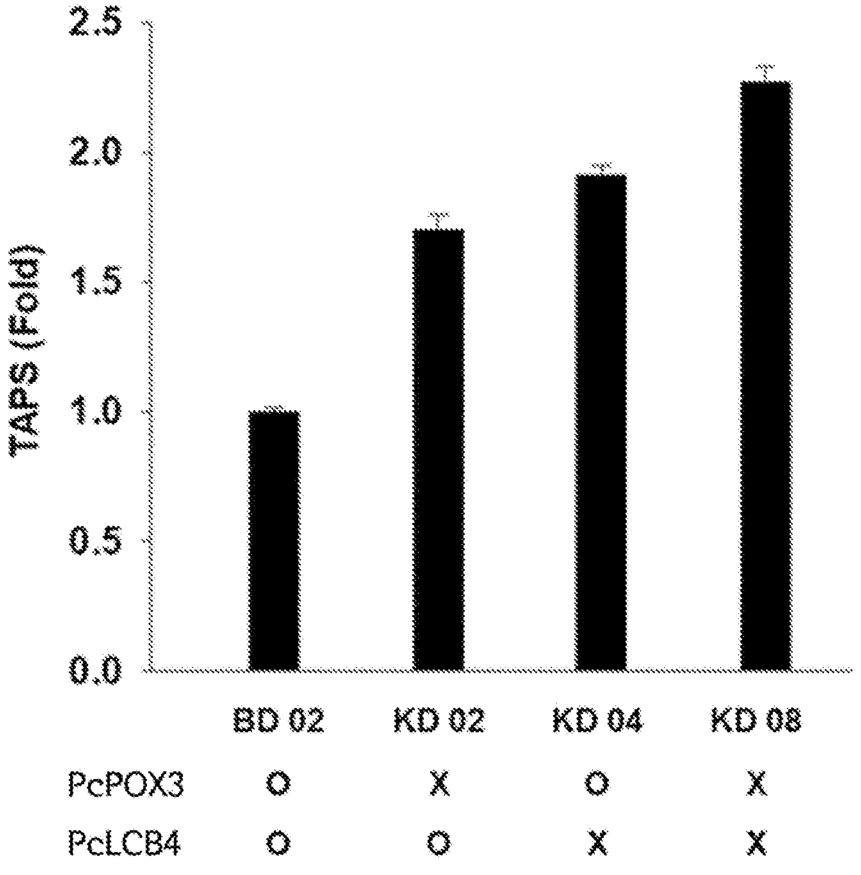
FIG. 3 is a graph showing TAPS production of each *Pichia ciferrii* mutant strain.
Figure 4:
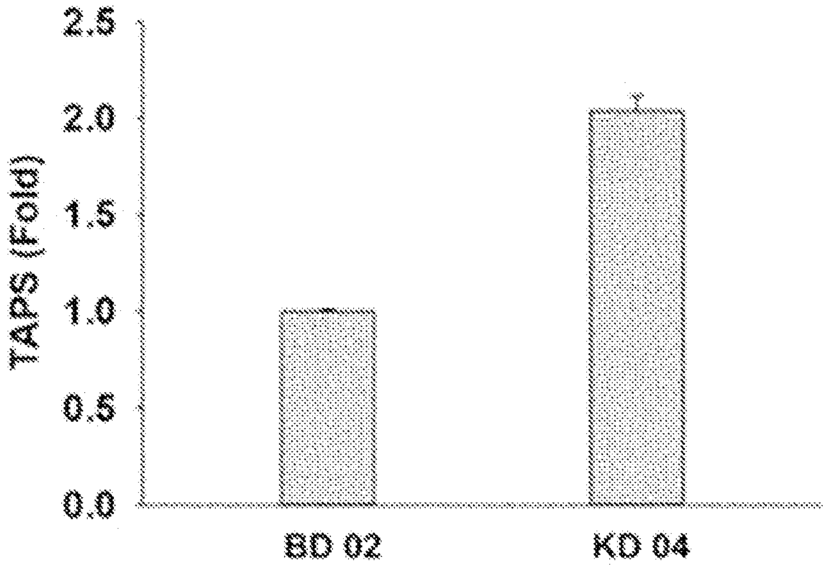
FIG. 4 is a graph showing TAPS production of the PcPOX3 gene-deleted *Pichia ciferrii* mutant strain in a medium containing C12 FAME.

As shown in Table 3 below and FIG. 3, when the YGM optimal medium was used, the TAPS-specific yields of the PcLCB4 gene-deleted mutant strain (KD 02) and the PcPOX3 gene-deleted mutant strain (KD 04) relative to BD 02 increased 1.9-fold and 1.7-fold, respectively.

In addition, the PcLCB4 and PcPOX3 genes-co-deleted mutant strain (KD 08) relative to BD 02 showed a 2.3-fold higher TAPS-specific yield.

TABLE 3

Results of analysis of TAPS production for each strain

| | BD 02 | KD 02 | KD 04 | KD 08 |
|---|---|---|---|---|
| TAPS (mg/L) | 2460 | 3750 | 2800 | 3500 |
| TAPS-specific yield (mg/DCW) | 10.9 | 20.85 | 18.53 | 24.72 |
| Relative TAPS-specific yield (based on BD 02) | 1 | 1.9 | 1.7 | 2.3 |

<Example 5> Addition of Fatty Acid Methyl Ester and Production of TAPS in Transformant Strains Each of the BD 02 and KD 04 transformant strains was inoculated into 50 ml of YGM optimal medium and cultured at 25° C. for 3 days at 220 rpm, and then, 50 ml of fatty acid-containing medium (glycerol 30 g/l, yeast extract 2 g/l, $KNO_3$ 3 g/l, $(NH_4)_2SO_4$ 0.5 g/l, $MgSO_4 \cdot 7H_2O$ 0.3 g/l, NaCl 0.5 g/l, CSL 3 g/l, LS-300 1 g/l, lauric acid methyl ester 2.14 g/l, and Tween 80 0.5%) was added thereto and cultured at 25° C. for 4 days at 220 rpm.

4 volumes of methanol was added thereto and reacted at room temperature for 1 hour, and then, the centrifuged supernatant was analyzed for TAPS.

TAPS was analyzed by HPLC using UV 200 nm. An 84.5:18.45:0.05 (w/w) mixture of methanol, water and TFA was used as a solvent.

As can be compared from the results in Table 4, when the optimal medium containing fatty acid methyl ester was used, the TAPS production of the PcPOX3-deleted mutant strain KD 04 relative to BD 02 increased by about 70% and the specific yield increased by 100% or more.

TABLE 4

Results of analysis of TAPS production for each strain

| | BD 02 | KD 04 |
|---|---|---|
| TAPS (mg/L) | 2240 | 3774 |
| TAPS-specific yield (mg/DCW) | 14.1 | 29 |
| Relative TAPS-specific yield (based on BD 02) | 1 | 2.1 |

The invention claimed is:

1. A *Pichia ciferrii* mutant strain genetically engineered to produce tetraacetyl phytosphingosine (TAPS) by intracellular palmitoyl-CoA accumulation induced by blocking β-oxidation of palmitoyl-CoA in a wild-type *Pichia ciferrii* strain, said blocking being obtained by introducing a deletion or insertion to disrupt a gene related to the β-oxidation of palmitoyl-CoA to suppress or decrease its expression, wherein the gene is a PcPOX3 gene that comprises SEQ ID NO: 28, wherein the genetically engineered *Pichia ciferrii* mutant strain exhibits increased TAPS specific yield when cultured in a medium supplemented with a fatty acid methyl ester (FAME) as compared to the same strain cultured without the FAME under the same conditions.

2. The *Pichia cifernii* mutant strain according to claim 1, wherein the genetically engineered *Pichia ciferrii* mutant strain comprises partial or total deletion of the gene, insertion of foreign DNA, replacement of a part of the gene with a foreign gene, or a combination thereof.

3. The *Pichia ciferri* mutant strain according to claim 2, wherein the genetically engineered *Pichia ciferrii* mutant strain comprises partial or total deletion of the gene.

4. The *Pichia ciferrii* mutant strain according to claim 3, wherein expression of a PcLCB4 gene that comprises SEQ ID NO: 29 is further suppressed by introducing a deletion or insertion to disrupt said PcLCB4 gene.

5. A method for producing tetraacetyl phytosphingosine (TAPS), comprising the steps of:

(a) culturing the *Pichia ciferrii* mutant strain according to claim 1 in a medium containing a carbon source; and (b) obtaining TAPS accumulated in the cultured *Pichia ciferrii* mutant strain.

6. A method for producing tetraacetyl phytosphingosine (TAPS), comprising the steps of:

(a) culturing the *Pichia ciferrii* mutant strain according to claim 1 in a medium containing a fatty acid methyl ester (FAME); and (b) obtaining TAPS accumulated in the cultured *Pichia ciferrii* mutant strain.

7. The method for producing TAPS according to claim 6, wherein the FAME is C12:0 methyl laurate.

8. A method for producing tetraacetyl phytosphingosine (TAPS), comprising the steps of:

(a) culturing the *Pichia ciferrii* mutant strain according to claim 4 in a medium containing a carbon source; and (b) obtaining TAPS accumulated in the cultured *Pichia ciferrii* mutant strain.

9. A method for producing tetraacetyl phytosphingosine (TAPS), comprising the steps of:

(a) culturing the *Pichia ciferrii* mutant strain according to claim 4 in a medium containing a fatty acid methyl ester (FAME); and (b) obtaining TAPS accumulated in the cultured *Pichia ciferrii* mutant strain.

10. The method for producing TAPS according to claim 9, wherein the FAME is C12:0 methyl laurate.

* * * * *

SEQUENCE LISTING

<160> NUMBER OF SEQ ID NOS: 29

<210> SEQ ID NO 1
<211> LENGTH: 1647
<212> TYPE: DNA
<213> ORGANISM: Pichia ciferrii
<220> FEATURE:
<221> NAME/KEY: gene
<222> LOCATION: (1)..(1647)
<223> OTHER INFORMATION: GAPDH, glyceraldehyde 3-phosphate dehydrogenase (GAPDH) gene

<400> SEQUENCE: 1
aagcaattaa acaacatacc aacaaaacaa ttatacccag tgatacctac atacaattaa 60
cccatagtaa actaatacct cacaacatta ataaagcatc tgatcttaat gtactactaa 120
tcctaaactc atgataatta ctgctgttgt aatgtttgtc atcactttga tcatcacgag 180
catcaccgga ccgttaatta ccaacaatct caattgtaga acacagtgtt aaacagggat 240
aaaacaacaa ttaattatga taaaaggttc aaacaagtac caatagatag ataattatta 300
cctctataat atatcattta attgaattaa tatcaatagt tgttattcaa ttatccctac 360
tttcctggtt aaagttacac catcagatgg ttcaccacca atgttgttca aaccatttcc 420
actcaactga cgtttcaaca acatcacctg aaaaaaaaat tcatcacaca ttgggagaaa 480
ttgggagaat tgtatataag gagttgaaat cgctaattat tttatacttc ttcattatac 540
ttctattcta catcagtatt ttataataca aaaacaaaca aataaaacaa ataattaaca 600
atggctatca cagttggtat taacggtttc ggtcgtattg gtcgtttagt cctaagaatt 660
gctctttcaa gaaaagatat tcaaattgtt gcaattaatg atccattcat tgcaccagaa 720
tatgcttcat atatgtttaa atatgattct actcatggtc gttatgcagg tgaagtttct 780
catgaaggtg ataacattgt tattgatggt aaaaaaatca gagtttatca agaacgtgat 840
ccagttaaca tcccatgggg taaagatggt gttgattatg ttattgattc aactggtgtt 900
tttaaagaat tagattctgc tcaaaaacat attgatgccg gtgctaaaaa agttgttatt 960
actgctccat catcaactgc tccaatgttt gttgttggtg ttaatgaaga taaatatact 1020
ccagatttaa acattatttc aaatgcttca tgtacaacaa attgtttagc tccattagct 1080
aaaattatta acaacaaatt tggtattgaa gaaggtttaa tgactactgt tcattcaatt 1140
actgctactc aaaaaactgt tgatggtcca tctcataaag attggagagg tggtcgtact 1200
gcttcaggta atattattcc atcatcaact ggtgctgcta aagctgttgg taaagttatt 1260
ccagaattag ctggtaaatt aactggtatg tctttaagag ttccaactgt tgatgtttca 1320
gttgttgatt taactgttaa attattaaaa gatgccactt atgatgaaat taaagctgct 1380
gttaaagaag ctgctgaagg tccattaaaa ggtgttgttg gttatactga agatcaagtt 1440
gtttcttcag atttcttgac tgataacaga tcatcaattt tcgatgctga agctggtatt 1500

```
tggttatcac caagatttgt taaattaatt gcttggtatg ataatgaata tggttactct   1560

accagagttg ttgatttatt agaatacgtt gcttcaaaaa ctaagaaacg aaagctaatg   1620

aaaagcaata gctttgaatt agtttga                                       1647


<210> SEQ ID NO 2
<211> LENGTH: 576
<212> TYPE: DNA
<213> ORGANISM: Artificial Sequence
<220> FEATURE:
<223> OTHER INFORMATION: nat1

<400> SEQUENCE: 2

atgggtacta ctttagatga tactgcttat agatatagaa cttcagttcc aggtgatgct     60

gaagctattg aagctttaga tggttcattt actactgata ctgtttttag agttactgct    120

actggtgatg gttttacttt aagagaagtt ccagttgatc caccattaac taaagttttt    180

ccagatgatg aatcagatga cgagtctgat gacggtgaag atggtgatcc agattcaaga    240

acttttgttg cttatggtga tgacggagac ttagctggtt ttgttgttgt ttcatattca    300

ggttggaata gaagattaac tgttgaagat attgaagttg ctccagaaca tagaggtcat    360

ggtgttggta gagctttaat gggtttagct actgaatttg ctagagaacg tggtgctggt    420

catttatggt tagaagttac taatgttaat gctccagcta ttcatgctta tagaagaatg    480

ggtttcacat tatgtggttt agatactgct ttatatgatg gtactgcttc agatggtgaa    540

caagctttat atatgtcaat gccatgtcca taataa                              576


<210> SEQ ID NO 3
<211> LENGTH: 1591
<212> TYPE: DNA
<213> ORGANISM: Pichia ciferrii
<220> FEATURE:
<221> NAME/KEY: gene
<222> LOCATION: (1)..(1591)
<223> OTHER INFORMATION: URA3, orotidine-5'-phosphate decarboxylase
      (URA3) gene

<400> SEQUENCE: 3

gattgatttg atatagattt gagctttgta gttctgatct attaggtaca aaaggtcttt     60

caatggcaaa agtgtacttt tttgattttt caatgaagtc gaaaaggttc aaattttttt    120

tgtcaacaaa acatcataaa tacccggatt tggcaagtat cccgatatgg tcatactcag    180

gaaccaattg atatcattat ttatttaggc attaaagtgt gaataattct ttgtgatatc    240

agtactttat tatatcaagc ttgaaaggga tactaggtga tccattgatc gaatctgctc    300

ttcttttcaa ccttctcaaa gaaacaaaat tgttgcttaa ttttggctgt tgtagaactt    360

gtacgggaca cgcttctatg aacaaatttg tccgatgagt tggataaata ttactttcct    420

ttgattgata gcacatcatc aatagattgc aaatataatc caaaatggtc accacattat    480

cttacactca aaggcagaag ctcacccttc tccattggca aagcgtttat tcaatgtcat    540

ggaatcaaaa aagtcaaact tgtgtgcttc aattgatgtt agaactacaa aagaattttt    600

acaattagtt gacacattag gtccatatat ctgtcttgtc aaaactcata tcgatattat    660

tgatgatttc tcatttgaag gtactatcaa accattgaga gaattagcac aaaagcacaa    720

ttttttaatc tttgaagatc gtaaatttgc tgatataggg aacacagtca aagcacaata    780

tgcaggtggt gctttcaaaa ttgcaacttg gtctgatatc acaaatgctc atggtgttac    840

tggtgctggt atcgttagtg ggttgaaaga ggctgctaaa gaagcttcag atgaaccaag    900
```

```
aggtttgttg atgttggctg aattgagttc aaaaggttca ttagccaaag gtgaatatac     960
taaacaaact gttgatatcg ctaaaactga taaagatttt gttattggat ttattgctca    1020
aaatgatatg ggtggtagag atgaaggctt tgattggtta atcatgaccc aggtgttggt    1080
cttgatgata aaggtgatgc cttaggtcaa caatatagat ctgttgatac tgtcgtttca    1140
actggtagtg atatcattat tgtcggtaga ggtttattcg gtaaaggaag agatccaaat    1200
gctgaaggtg aacgttacag agctgctggt tggaatgctt atttgaaaag aactggtcaa    1260
atatagaatg tagtttaaat ataaaatatt agactaaata attaatgggt gctagtttgt    1320
aactagttca acgactataa ttaactgaca ttaaaagtag ctgactctaa gtgtattcaa    1380
tgtcattcat actgctaatc aaataaatca aaatatacat tgaagtttgt atcattaatt    1440
agaagatgtt ataatgtcga tgactaagca agtaaattaa aaccgaaatc catctgtatg    1500
taaaaatact tcaaagtctt aacagcatag atagaagctt atcaatcaac tatcatcaag    1560
ccagtagatg ccattcaaaa gtgacaaatg t                                    1591
```

```
<210> SEQ ID NO 4
<211> LENGTH: 2983
<212> TYPE: DNA
<213> ORGANISM: Artificial Sequence
<220> FEATURE:
<223> OTHER INFORMATION: Artificial cassette (PcURA3)

<400> SEQUENCE: 4
```

```
tgagaaacgt ggcaatggat cattgtttat agaaaaattt aatgaatacg acaataatat      60
taaaacaatt taatactgaa ataaaagttg taatatagta taaaatataa aattcatgag     120
aaatatgtac aaaaggtttg taagatcacc acattttctt taaaatgatc tcaccataat     180
aataaaacat ctaaagataa atcaaaggga acccacaaat tgaaatgaaa agaattgtat     240
aaacatcatg actttaaaca attcacttct agtatatgag agataataaa ttcattaaca     300
gtattttttt tttctaaatt ttttaatttt ttgtatctaa attctttaag caaacaagaa     360
taaaagatta atacacctat taaatatctg aaccttaacg tctcatttgt tgagttaata     420
aagcattttg ttcttggaat ctttgaccga ctctttcact gtgtttcaag aatttttcag     480
aacattttaa aacacatgta ttttcttttg aagttaatga agcggaagtg aaatcattaa     540
cacaatcatt gaaacaacgt tcaaccaagt ttgagtaaag acgcatgaaa tctttcattt     600
gtttaccttc aacgattctt tggaaatctt gttgttctct ttggtttaat tgatccattt     660
tgattgattt gatatagatt tgagctttgt agttctgatc aattaggtac aaaaggtctt     720
tcaatggcaa aagtgtactt ttttgatttt tcaatgaagt cgaaaaggtt caaatttttt     780
tttggtcaac aaaacatcat aaatatccga atttggaaag attcccgata tggacaaaat     840
caggaatcaa ttggaattat gattcatttg agcattatag tgtgaataat tctttatgtt     900
ctctgttctt tattatatca agctttaaag agacactagg cgtcccatag atcggatggt     960
ctattcaagt gtctcaaaga aaaaaaatag ttgcttgatt ttggctgtag tagagcttgt    1020
acgggacacg cttctatgaa taaatttgtc cgatgagttg gataaatatt aactgaacta    1080
atttcttcta attgatagag catcatcaat atattgcaca taatataatt caaaaaaaca    1140
acaaacaaca acaactttac ccagtggtac ctacatacaa ttgacccata gtaaactaat    1200
aactcataac acaataaagc atctgatctt aatgtactac taaatactaa actgatgata    1260
attacttttg ttgtaatgtt tgtcatcact ttgatcatca cgagcatcac cggaccgtta    1320
attaccaaca atctcaattg tacaacatag tgttaaaaca ggataacttg atgattatat    1380
```

gtgatattaa gttcaaacaa gtaccaataa atagataatt aatagctcta taatatatca 1440
tttaattgaa ttaatatcaa tagttgttgt ttaattatcc ctagttttct ggttaaagtt 1500
acaccatcag atggttcacc accaatgttg ttcaaaccat ttccactcaa ctgacgtttc 1560
cagaacatca ccctgaaaaa aaaaaattca tcacacattg ggagaaattg gggaggattg 1620
tatataagga gtggaaattc gctaatattt ttataattct aactcacttg ttttaattca 1680
acatcagtat tttataatac aaaaacaaac aaacaaacaa ataattaatt aacaatgggt 1740
actactttag atgatactgc ttatagatat agaacttcag ttccaggtga tgctgaagct 1800
attgaagctt tagatggttc atttactact gatactgttt ttagagttac tgctactggt 1860
gatggtttta ctttaagaga agttccagtt gatccaccat taactaaagt tttccagat 1920 gatgaatcag atgacgagtc tgatgacggt gaagatggtg atccagattc aagaactttt 1980
gttgcttatg gtgatgacgg agacttagct ggttttgttg ttgtttcata ttcaggttgg 2040
aatagaagat taactgttga agatattgaa gttgctccag aacatagagg tcatggtgtt 2100
ggtagagctt taatgggttt agctactgaa tttgctagag aacgtggtgc tggtcattta 2160
tggttagaag ttactaatgt taatgctcca gctattcatg cttatagaag aatgggtttc 2220
acattatgtg gtttagatac tgctttatat gatggtactg cttcagatgg tgaacaagct 2280
ttatatatgt caatgccatg tccataataa gttgactgat ttataatttt attattatta 2340
tttcaattct tattttttat cattaggtat taatgtggat tatgttttaa cttgttaata 2400
tataaattca cataaactaa taattgtaga tttttcgtta tcattgaaaa gcgtatacta 2460
ttaattatga ccccaggtgt tggtcttgat gataaaggtg atgccttagg tcaacaatat 2520
agatccgttg ataccgttgt ttcaactggt agtgatatca ttattgttgg tagaggtttg 2580
ttcggtaaag gaagagatcc aaatgctgaa ggtgaacgtt acagagctgc tggttggaat 2640
gcctatttga aaagaactgg tcaaatatag tatgtagttt aaatctaaca tattagacta 2700
aataattaat gggtcataat ttgtaattag ttcaacgact aactaactga cattagaagg 2760
aagactctaa ttgtatacca tgtcatcaat actcctaatt atcaaataaa tcaaaatata 2820
taccttctat cattaattag aagatgtaat gtcgatgact aagcaagata aattaaaacc 2880
gaaatccatc tgtatgtaaa aatactttca agtaattacc acatagatag aagctcacca 2940
accaactatc atcaagccag tagatgccat tcaagagtga caa 2983

<210> SEQ ID NO 5
<211> LENGTH: 2289
<212> TYPE: DNA
<213> ORGANISM: Artificial Sequence
<220> FEATURE:
<223> OTHER INFORMATION: Artificial cassette (PcPOX3 cassette 1)

<400> SEQUENCE: 5
agtatcaaat caattactta tacacttatg acttttatga cttttaaacg ggtgatttct 60
cttggacttt cgaggaacat gctctaaatc aagcagagat cacaaatatt ttaataacta 120
atgaataatt ttaaaattaa aggacttgta gcatattttg tggaatttcc ccatagttta 180
ttaatgtttt tggaacctcg gctttaatgg gccctgcaca aatccgacgg tccccaattg 240
cacaaatccg acggcagcca atttgtttat aaaagaaaag gaaaatcctt taatttcaaa 300
tccaaaacat caacaaaaaa gttggatctc aattggaaat aggctgggaa tcactgggaa 360
atgagtgcac aggagtcaga taggttgatc caggaaaggg ccattgagag ggctggaacc 420

```
tcttttaacg tccaggattt gattcattat ttagatgatg gagaggaaaa tactaaaatt    480

tatgaatcaa tgtcacttca attagaaaga gatccaattt ttaaaattaa atcttcacat    540

ttagatttaa aagccaaaag agaattagct ttcaaaaaaa ttgtgaaatt agctggttat    600

ggtcaacaat atagatccgt tgataccgtt gtttcaactg gtagtgatat cattattgtt    660

ggtagaggtt tgttcggtaa aggaagagat ccaaatgctg aaggtgaacg ttacagagct    720

gctggttgga atgcctattt gaaaagaact ggtcaaatat agtatgtagt ttaaatctaa    780

catattagac taaataatta atgggtcata atttgtaatt agttcaacga ctaactaact    840

gacattagaa ggaagactct aattgtatac catgtcatca atactcctaa ttatcaaata    900

aatcaaaata tataccttct atcattaatt agaagatgta atgtcgatga ctaagcaaga    960

taaattaaaa ccgaaatcca tctgtatgta aaaatacttt caagtaatta ccacatagat   1020

agaagctcac caaccaacta tcatcaagcc agtagatgcc attcaagagt gacaaatgtc   1080

attggaaaat gagttcacag gatcctcctt tgagaatgag tttgaaaata ctactgccca   1140

accagaattc tgcagaatta attcgccctt ttttttggt caacaaaaca tcataaatat   1200

ccgaatttgg aaagattccc gatatggaca aaatcaggaa tcaattggaa ttatgattca   1260

tttgagcatt atagtgtgaa taattcttta tgttctctgt tctttattat atcaagcttt   1320

aaagagacac taggcgtccc atagatcgga tggtctattc aagtgtctca aagaaaaaaa   1380

atagttgctt gattttggct gtagtagagc ttgtacggga cacgcttcta tgaataaatt   1440

tgtccgatga gttggataaa tattaactga actaatttct tctaattgat agagcatcat   1500

caatatattg cacataatat aattcaaaat ggttaccaca ttatcttatt ctcaaagagc   1560

agaagctcac ccttctccat tggcaaagcg tttattcaat gttatggaat caaaaaagtc   1620

aaacttgtgt gcttcaattg atgttagaac tacaaaagaa tttttacaat tagttgacac   1680

attaggtcca tatatctgtc ttgtcaaaac tcatatcgat attattgatg atttctcatt   1740

cgaaggtacc attaaaccat tgaaagaatt agcacaaaag cacaattttt taatctttga   1800

agatcgtaaa tttgctgata tagggaacac agtcaaagca caatatgcag gtggtgcttt   1860

caaaattgca acttggtctg atatcacaaa tgctcatggt gttactggtg ctggtatcgt   1920

tagtggattg aaagaagctg ctaaagaagc ttctgatgaa ccaagagggt tgttgatgtt   1980

ggctgaattg agttcaaaag gttcattagc caaaggtgaa tatactaaac aaactgttga   2040

tatcgctaaa actgataaag atttcgttat tggttttatt gctcaaaatg atatgggtgg   2100

tagagatgga ggctttgatt ggttaattat gaccccaggt gttggtcttg atgataaagg   2160

tgatgcctta ggtcaacaat atagatccgt tgataccgtt gtttcaactg gtagtgatat   2220

cattattgtt ggtagaggtt tgttcggtaa aggaagagat ccaaatgctg aaggtgaacg   2280

ttacagagc                                                           2289
```

<210> SEQ ID NO 6
<211> LENGTH: 1671
<212> TYPE: DNA
<213> ORGANISM: Artificial Sequence
<220> FEATURE:
<223> OTHER INFORMATION: Artificial cassette (PcPOX3 cassette 2)

<400> SEQUENCE: 6

```
tttccattac atcagaaaac atttcacaat tttattcatt caatatagtt aaaggttcag     60

attttttgga aaatttaaat tataaaattg atgaaattaa tgaattatta agacctgata    120

ttattggatt aactgatgct ttcaatttat cagattttgt aattgattct caaattggga    180
```

aaagaaatgg tgatatttat gaatcttatt tcaaacatgt taatgataat aattctgatt 240
tgaaacctca ttattatgat tctatcatga aacctttttt ccaaagagat atgaaaccta 300
gtgataatga agaagttgat gaggaggagg aagaatagct acacacacca acctctcaac 360
aacttattat acattcttct tgacttttct atgactttta tagctttaaa taaattcaaa 420
tttgatactt tatactgatt acgtaataca aattccccg gtaaacacac acttttttt 480
gtttactttt caaaacatca acaaaaaatt taaaacactt tgaacgccaa aaaagaagga 540
aaaggaaaac catcaaaaag atcgattgaa gaagaagtta gaaggatatt aaggaaatat 600
attaggtcca tatatctgtc ttgtcaaaac tcatatcgat attattgatg atttctcatt 660
cgaaggtacc attaaaccat tgaaagaatt agcacaaaag cacaattttt taatctttga 720
agatcgtaaa tttgctgata tagggaacac agtcaaagca caatatgcag gtggtgcttt 780
caaaattgca acttggtctg atatcacaaa tgctcatggt gttactggtg ctggtatcgt 840
tagtggattg aaagaagctg ctaaagaagc ttctgatgaa ccaagagggt tgttgatgtt 900
ggctgaattg agttcaaaag gttcattagc caaaggtgaa tatactaaac aaactgttga 960
tatcgctaaa actgataaag atttcgttat tggttttatt gctcaaaatg atatgggtgg 1020
tagagatgga ggctttgatt ggttaattat gaccccaggt gttggtcttg atgataaagg 1080
tgatgcctta ggtcaacaat atagatccgt tgataccgtt gtttcaactg gtagtgatat 1140
cattattgtt ggtagaggtt tgttcggtaa aggaagagat ccaaatgctg aaggtgaacg 1200
ttacagagct gctggttgga atgcctattt gaaaagaact ggtcaaatat agtatgtagt 1260
ttaaatctaa catattagac taaataatta atgggtcata atttgtaatt agttcaacga 1320
ctaactaact gacattagaa ggaagactct aattgtatac catgtcatca atactcctaa 1380
ttatcaaata aatcaaaata tataccttct atcattaatt agaagatgta atgtcgatga 1440
ctaagcaaga taaattaaaa ccgaaatcca tctgtatgta aaaatacttt caagtaatta 1500
ccacatagat agaagctcac caaccaacta tcatcaagcc agtagatgcc attcaagagt 1560
gacaaatgtc attggaaaat gagttcacag gatcctcctt tgagaatgag tttgaaaata 1620
ctactgccca accagaatta agggcgaatt ccagcacact ggcggccgtt a 1671

<210> SEQ ID NO 7
<211> LENGTH: 2799
<212> TYPE: DNA
<213> ORGANISM: Artificial Sequence
<220> FEATURE:
<223> OTHER INFORMATION: Artificial cassette (PcLCB4 cassette 1)

<400> SEQUENCE: 7
aaacttattc tcttgtttgg aacacattac aacacatttt agttaaagtc ttgttggcga 60
aactggtatc aagaaaacgt ttcacaactt tatcattttg atataaagac atacttcaac 120
ccatccatac acttatttga actctttttt gcccttttca tcatgccgag ttttgactct 180
caaagaatta aactgatgga tacagtatca gtaaaccccc aagagccatc attggtgata 240
caggtatcat cattaaagat caatcttcat tctattacaa tcaacatgat aacgcttcat 300
tttcatcttg cttaagttgc tcttcatcaa actcgaatgg tacggtgaaa tcttcaggtc 360
caaaacatat tccatttgtt gatatattga gtgttcgata tataaatgaa aataatgaat 420
ctttattaga agctggaagt tccactgtga ctagtgatga acctgatgtc gaagtggtat 480
ttgttagaca aaagggtaaa actcttgtac caactccaat aatattatca atagatactt 540

```
taggtcatga tgatgttgta caagaaattt ggagattaag ttatcaagga acaaaccaag    600
aaaatcaata ttagttcttg ttaatccaca tggtgggaaa ggtaaagcta taaattcatt    660
ctaactcaat caaaacctgt attaattggt gctcaagctt ctgttgaagt tagacatact    720
caatattatc aacatgctac agatattgca cgcactttga atattgataa atatgatata    780
attgcatgtg cttcaggtga tggtgtccca catgaagtct tgaatggatt ttatcaaaga    840
tctgatagag ctgaagcttt caataagatt acaataactc aattaccatg tggttcaggt    900
aatgcaatga gtgaatcatg tcatggtaca aataatccaa gttttgccgc tctatcatta    960
ttgaaatcaa gtacggtaaa tttagattta atggcttgta cacaaggtga taaaacttat   1020
gtttcattct taagtcaaac tgtcggtgtt atagcagatt ctgatattgg tactgaagca   1080
cttagatggt taggtccttc aagatttgaa ggtcaacaat atagatccgt tgataccgtt   1140
gtttcaactg gtagtgatat cattattgtt ggtagaggtt tgttcggtaa aggaagagat   1200
ccaaatgctg aaggtgaacg ttacagagct gctggttgga atgcctattt gaaaagaact   1260
ggtcaaatat agtatgtagt ttaaatctaa catattagac taaataatta atgggtcata   1320
atttgtaatt agttcaacga ctaactaact gacattagaa ggaagactct aattgtatac   1380
catgtcatca atactcctaa ttatcaaata aatcaaaata tataccttct atcattaatt   1440
agaagatgta atgtcgatga ctaagcaaga taaattaaaa ccgaaatcca tctgtatgta   1500
aaaatacttt caagtaatta ccacatagat agaagctcac caaccaacta tcatcaagcc   1560
agtagatgcc attcaagagt gacaaatgtc attggaaaat gagttcacag gatcctcctt   1620
tgagaatgag tttgaaaata ctactgccca accagaattc tgcagaatta attcgccctt   1680
tttttttggt caacaaaaca tcataaatat ccgaatttgg aaagattccc gatatggaca   1740
aaatcaggaa tcaattggaa ttatgattca tttgagcatt atagtgtgaa taattcttta   1800
tgttctctgt tctttattat atcaagcttt aaagagacac taggcgtccc atagatcgga   1860
tggtctattc aagtgtctca aagaaaaaaa atagttgctt gattttggct gtagtagagc   1920
ttgtacggga cacgcttcta tgaataaatt tgtccgatga gttggataaa tattaactga   1980
actaatttct tctaattgat agagcatcat caatatattg cacataatat aattcaaaat   2040
ggttaccaca ttatcttatt ctcaaagagc agaagctcac ccttctccat tggcaaagcg   2100
tttattcaat gttatggaat caaaaaagtc aaacttgtgt gcttcaattg atgttagaac   2160
tacaaaagaa tttttacaat tagttgacac attaggtcca tatatctgtc ttgtcaaaac   2220
tcatatcgat attattgatg atttctcatt cgaaggtacc attaaaccat tgaaagaatt   2280
agcacaaaag cacaattttt taatctttga agatcgtaaa tttgctgata tagggaacac   2340
agtcaaagca caatatgcag gtggtgcttt caaaattgca acttggtctg atatcacaaa   2400
tgctcatggt gttactggtg ctggtatcgt tagtggattg aaagaagctg ctaaagaagc   2460
ttctgatgaa ccaagagggt tgttgatgtt ggctgaattg agttcaaaag gttcattagc   2520
caaaggtgaa tatactaaac aaactgttga tatcgctaaa actgataaag atttcgttat   2580
tggttttatt gctcaaaatg atatgggtgg tagagatgga ggctttgatt ggttaattat   2640
gaccccaggt gttggtcttg atgataaagg tgatgcctta ggtcaacaat atagatccgt   2700
tgataccgtt gtttcaactg gtagtgatat cattattgtt ggtagaggtt tgttcggtaa   2760
aggaagagat ccaaatgctg aaggtgaacg ttacagagc                           2799
```

<210> SEQ ID NO 8
<211> LENGTH: 2278

-continued

<212> TYPE: DNA
<213> ORGANISM: Artificial Sequence
<220> FEATURE:
<223> OTHER INFORMATION: Artificial cassette (PcLCB4 cassette 2)

<400> SEQUENCE: 8
cgtatggcac caactttatt atcattagat caaggttctc atgttttaca accagaagtt 60
caacattcta aaataatagc atatagatta actccaaagc agcaacatgg ttatttaagt 120
gttgatggtg aaagttatcc atttgaaact attcaagttg aaattctacc cggtgctgca 180
aagactttac taagaaatgg tacttatgtt gaaacaaatt tttattgaaa tgaatgataa 240
attttgatgc ttacatatat atatatatta tctctaacga atgaaacgaa tatgatactt 300
acaatctgat tacacaaata tttaattgta gtcaacttat aattgttgaa tttaaaattt 360
gatttaattt ttgaagcttt aatggagatg ccgatgttgg ataaaccggg ttttgaaaat 420
ctttttgact ccatactaaa aaattaagtg ctgatgagta acttaaggaa cgtcaagtca 480
tagaagtaat tgttttattt caaattttta taaattaagc gctttttcct tcagttgttt 540 ttttttgtt ggtttattta ttactcaaaa atttctaaat aataacataa attatagaaa 600
tcatgagtga agacgaacaa gaatttgcta aattagaaca aactttacca gactcaatca 660
agagttcatc atcacatatt ttcaatcaag aatttttaaa ttcaattaat catactccat 720
cattaactcc acaaagttca ataccgccag aatcaccaaa attgccaaag aaaactccat 780
taagtaattt taaagatgaa ttatataaaa atggtgatgt cgaaagaacc cattcaccaa 840
ttccaacacc aggtccttta cttcatcctg atgttcattt cccagctttg aataagcaaa 900
atgcagctac tggtgttatt tggtgtactg atcgtgcaaa tgaacgtggt ttcccaaatc 960
caaattgggt caatttaggt caaggtatgc cagaaacagg tgatattcca ggatgttttg 1020
ataggccaaa atcaatgaat atttcaattg aatctcgtga atatggtcca acatctggta 1080
ttaaaccttt aagacaagct attgcaaatt tatataatga acattataga caaggtaaag 1140
aatcaaaata tacttgggaa aatgtcaatg ttgcaccagg tggcagagct gctttaacaa 1200
gaattgcatt aggtccatat atctgtcttg tcaaaactca tatcgatatt attgatgatt 1260
tctcattcga aggtaccatt aaaccattga aagaattagc acaaaagcac aattttttaa 1320
tctttgaaga tcgtaaattt gctgatatag ggaacacagt caaagcacaa tatgcaggtg 1380
gtgctttcaa aattgcaact tggtctgata tcacaaatgc tcatggtgtt actggtgctg 1440
gtatcgttag tggattgaaa gaagctgcta aagaagcttc tgatgaacca agagggttgt 1500
tgatgttggc tgaattgagt tcaaaaggtt cattagccaa aggtgaatat actaaacaaa 1560
ctgttgatat cgctaaaact gataaagatt tcgttattgg ttttattgct caaaatgata 1620
tgggtggtag agatggaggc tttgattggt taattatgac cccaggtgtt ggtcttgatg 1680
ataaaggtga tgccttaggt caacaatata gatccgttga taccgttgtt tcaactggta 1740
gtgatatcat tattgttggt agaggtttgt tcggtaaagg aagagatcca aatgctgaag 1800
gtgaacgtta cagagctgct ggttggaatg cctatttgaa aagaactggt caaatatagt 1860
atgtagttta aatctaacat attagactaa ataattaatg ggtcataatt tgtaattagt 1920
tcaacgacta actaactgac attagaagga agactctaat tgtataccat gtcatcaata 1980
ctcctaatta tcaaataaat caaaatatat accttctatc attaattaga agatgtaatg 2040
tcgatgacta agcaagataa attaaaaccg aaatccatct gtatgtaaaa atactttcaa 2100
gtaattacca catagataga agctcaccaa ccaactatca tcaagccagt agatgccatt 2160
caagagtgac aaatgtcatt ggaaaatgag ttcacaggat cctcctttga gaatgagttt 2220
gaaaatacta ctgcccaacc agaattaagg gcgaattcca gcacactggc ggccgtta 2278

<210> SEQ ID NO 9
<211> LENGTH: 23
<212> TYPE: DNA
<213> ORGANISM: Artificial Sequence
<220> FEATURE:
<223> OTHER INFORMATION: nat1_MB primer

<400> SEQUENCE: 9
ttcaacggtt aatctacggt tcc 23

<210> SEQ ID NO 10
<211> LENGTH: 25
<212> TYPE: DNA
<213> ORGANISM: Artificial Sequence
<220> FEATURE:
<223> OTHER INFORMATION: PcURA3_5D1F primer

<400> SEQUENCE: 10
tgagaaacgt ggcaatggat cattg 25

<210> SEQ ID NO 11
<211> LENGTH: 21
<212> TYPE: DNA
<213> ORGANISM: Artificial Sequence
<220> FEATURE:
<223> OTHER INFORMATION: nat1_1F primer

<400> SEQUENCE: 11
atgaccactt tggatgacac c 21

<210> SEQ ID NO 12
<211> LENGTH: 26
<212> TYPE: DNA
<213> ORGANISM: Artificial Sequence
<220> FEATURE:
<223> OTHER INFORMATION: PcURA3_3D2B primer

<400> SEQUENCE: 12
ttgtcactct tgaatggcat ctactg 26

<210> SEQ ID NO 13
<211> LENGTH: 20
<212> TYPE: DNA
<213> ORGANISM: Artificial Sequence
<220> FEATURE:
<223> OTHER INFORMATION: PCura3R primer

<400> SEQUENCE: 13
gctctgtaac gttcaccttc 20

<210> SEQ ID NO 14
<211> LENGTH: 25
<212> TYPE: DNA
<213> ORGANISM: Artificial Sequence
<220> FEATURE:
<223> OTHER INFORMATION: PCura3F primer

<400> SEQUENCE: 14
attaggtcca tatatctgtc ttgtc 25

<210> SEQ ID NO 15
<211> LENGTH: 54

<212> TYPE: DNA
<213> ORGANISM: Artificial Sequence
<220> FEATURE:
<223> OTHER INFORMATION: PcPOX3 N1

<400> SEQUENCE: 15
gatgcatgct cgagcagtat caaatcaatt acttatacac ttatgacttt tatg 54

<210> SEQ ID NO 16
<211> LENGTH: 39
<212> TYPE: DNA
<213> ORGANISM: Artificial Sequence
<220> FEATURE:
<223> OTHER INFORMATION: PcPOX3 N2

<400> SEQUENCE: 16
agtatcaaat caattactta tacacttatg acttttatg 39

<210> SEQ ID NO 17
<211> LENGTH: 49
<212> TYPE: DNA
<213> ORGANISM: Artificial Sequence
<220> FEATURE:
<223> OTHER INFORMATION: PcPOX3 N3

<400> SEQUENCE: 17
tatattgttg accgcataac cagctaattt cacaattttt ttgaaagct 49

<210> SEQ ID NO 18
<211> LENGTH: 45
<212> TYPE: DNA
<213> ORGANISM: Artificial Sequence
<220> FEATURE:
<223> OTHER INFORMATION: PcPOX3 N4

<400> SEQUENCE: 18
cactggcggc cgttatttcc attacatcag aaaacatttc acaat 45

<210> SEQ ID NO 19
<211> LENGTH: 49
<212> TYPE: DNA
<213> ORGANISM: Artificial Sequence
<220> FEATURE:
<223> OTHER INFORMATION: PcPOX3 N5

<400> SEQUENCE: 19
ccgagctcgg atccaatatt tccttaatat ccttctaact tcttcttca 49

<210> SEQ ID NO 20
<211> LENGTH: 34
<212> TYPE: DNA
<213> ORGANISM: Artificial Sequence
<220> FEATURE:
<223> OTHER INFORMATION: PcPOX3 N6

<400> SEQUENCE: 20
atatttcctt aatatccttc taacttcttc ttca 34

<210> SEQ ID NO 21
<211> LENGTH: 40
<212> TYPE: DNA
<213> ORGANISM: Artificial Sequence
<220> FEATURE:
<223> OTHER INFORMATION: PcLCB4 N1

<400> SEQUENCE: 21
gatgcatgct cgagcaaact tattctcttg tttggaacac 40

<210> SEQ ID NO 22
<211> LENGTH: 25
<212> TYPE: DNA
<213> ORGANISM: Artificial Sequence
<220> FEATURE:
<223> OTHER INFORMATION: PcLCB4 N2

<400> SEQUENCE: 22
aaacttattc tcttgtttgg aacac 25

<210> SEQ ID NO 23
<211> LENGTH: 38
<212> TYPE: DNA
<213> ORGANISM: Artificial Sequence
<220> FEATURE:
<223> OTHER INFORMATION: PcLCB4 N3

<400> SEQUENCE: 23
tatattgttg accgcttcaa atcttgaagg acctaacc 38

<210> SEQ ID NO 24
<211> LENGTH: 38
<212> TYPE: DNA
<213> ORGANISM: Artificial Sequence
<220> FEATURE:
<223> OTHER INFORMATION: PcLCB4 N4

<400> SEQUENCE: 24
cactggcggc cgttacgtat ggcaccaact ttattatc 38

<210> SEQ ID NO 25
<211> LENGTH: 37
<212> TYPE: DNA
<213> ORGANISM: Artificial Sequence
<220> FEATURE:
<223> OTHER INFORMATION: PcLCB4 N5

<400> SEQUENCE: 25
ccgagctcgg atccagcaat tcttgttaaa gcagctc 37

<210> SEQ ID NO 26
<211> LENGTH: 22
<212> TYPE: DNA
<213> ORGANISM: Artificial Sequence
<220> FEATURE:
<223> OTHER INFORMATION: PcLCB4 N6

<400> SEQUENCE: 26
gcaattcttg ttaaagcagc tc 22

<210> SEQ ID NO 27
<211> LENGTH: 150
<212> TYPE: DNA
<213> ORGANISM: Pichia ciferrii
<220> FEATURE:
<221> NAME/KEY: gene
<222> LOCATION: (1)..(150)
<223> OTHER INFORMATION: T-TEF

<400> SEQUENCE: 27
gttgactgat ttataatttt attattatta tttcaattct tattttttat cattaggtat 60
taatgtggat tatgttttaa cttgttaata tataaattca cataaactaa taattgtaga 120
tttttcgtta tcattgaaaa gcgtatacta 150

<210> SEQ ID NO 28
<211> LENGTH: 2049
<212> TYPE: DNA
<213> ORGANISM: Pichia ciferrii
<220> FEATURE:
<221> NAME/KEY: gene
<222> LOCATION: (1)..(2049)
<223> OTHER INFORMATION: POX3 gene

<400> SEQUENCE: 28
atgagtgcac aggagtcaga taggttgatc caggaaaggg ccattgagag ggctggaacc 60
tcttttaacg tccaggattt gattcattat ttagatgatg gagaggaaaa tactaaaatt 120
tatgaatcaa tgtcacttca attagaaaga gatccaattt ttaaaattaa atcttcacat 180
ttagatttaa aagccaaaag agaattagct ttcaaaaaaa ttgtgaaatt agctggttat 240
ttccaaaact ctgatgaagt tgaactacgt aatagaatta gaattctttc acttattgat 300
ccggatgttg ctacaagaat tggtgttcat tatgggttat tcattggtac tctaagagct 360
cttggttctt caaaacaatt tgaattttgg atcaagaaag gtgctttttc attatcaaat 420
ttttatggat gttttgcaat gactgaatta gctcatggtt ctaatgttgc agctttacaa 480
acaactgcaa cttatgatcc acaagatgaa acttttatca tccatacacc ttcattaagt 540
gctacaaaat ggtggattgg tggcgctgct cattcagcta ctcatgctgt tgtttatgct 600
agattaatct cccagggaaa ggattatggt gttaagaatt tcattgttca attaagaaat 660
tctcaacatg aattattacc aggtgtttca gttggtgata ttggtaaaaa aatgggtaga 720
gatggtattg ataatggttg gattcaattc acaaatgtta aaatccctaa attcaatatg 780
ttggataaat atgctaaagt tgataatgat ggtaaagtta cattacctca attccaacaa 840
ttaggttata ctgcattagt tgttggtaga gtctcaatgg ttgttgattc ttataacact 900
ggtaagaaat ttttaacaat tgcattaaga tatgcatcaa caagaagaca atttggtaaa 960
gattctgaag ggaaagagaa aaaaatcatt gattatacac atcatagaag aagattattc 1020
ccattattag ctagtgttta tgcaatgaat tcagctgctt tagttatttc aaaatttcaa 1080
gatgaagcta ataaacttgt tgaaagtggt gaaaatttaa aacatgtgat tccaaattta 1140
aaagatcttt ttggtctttc agctggatta aaggcatttt gtacttggga aactgctcat 1200
attattgatg aaacaagaca aagttgtggt ggtcatggtt attcagatta taatgctttt 1260
gcaagaggtt ataatgattg ggttgttcaa tgtacttggg aaggtgataa taatgtttta 1320
tcaatgagtt gtggtagagc tttaattcaa aattatctaa gtgttgaaaa gaagaaaatt 1380
gtggggaaat atacaaaata tttagaaacc acagatattt caaatgaatt tgaattaaaa 1440
tctcaagatt tagaatatat tgaaaaaata attaaagctt gggaatttgt ttctaagagt 1500
ttaattgtta aatcaacaaa taaatttaaa aattttgtta aagaatttaa tggtgatgtt 1560
gaattagcat ttgaaaaaat ctcatcatat agatttatta ttgctaaagt tcatacaaaa 1620
ttaatccttt tgaaatcatt ttatgaaaga attttggaag caccaaagaa tttaaaacca 1680
gttctgtcat tattattaca attatattct ctttccatta catcagaaaa catttcacaa 1740
ttttattcat tcaatatagt taaaggttca gatttttttgg aaaatttaaa ttataaaatt 1800
gatgaaatta atgaattatt aagacctgat attattggat taactgatgc tttcaattta 1860
tcagattttg taattgattc tcaaattggg aaaagaaatg gtgatattta tgaatcttat 1920
ttcaaacatg ttaatgataa taattctgat ttgaaacctc attattatga ttctatcatg 1980

-continued

```
aaacctttttt tccaaagaga tatgaaacct agtgataatg aagaagttga tgaggaggag   2040

gaagaatag                                                            2049


<210> SEQ ID NO 29
<211> LENGTH: 1530
<212> TYPE: DNA
<213> ORGANISM: Pichia ciferrii
<220> FEATURE:
<221> NAME/KEY: gene
<222> LOCATION: (1)..(1530)
<223> OTHER INFORMATION: LCB4 gene

<400> SEQUENCE: 29

atgccgagtt ttgactctca aagaattaaa ctgatggata cagtatcagt aaacccccca     60

agagccatca ttggtgatac aggtatcatc attaaagatc aatcttcatt ctattacaat    120

caacatgata acgcttcatt ttcatcttgc ttaagttgct cttcatcaaa ctcgaatggt    180

acggtgaaat cttcaggtcc aaaacatatt ccatttgttg atatattgag tgttcgatat    240

ataaatgaaa ataatgaatc tttattagaa gctggaagtt ccactgtgac tagtgatgaa    300

cctgatgtcg aagtggtatt tgttagacaa aagggtaaaa ctcttgtacc aactccaata    360

atattatcaa tagatacttt aggtcatgat gatgttgtac aagaaatttg gagattaagt    420

tatcaaggaa caaaaccaag aaaatcaata ttagttcttg ttaatccaca tggtgggaaa    480

ggtaaagcta taaattcatt cttaactcaa tcaaaacctg tattaattgg tgctcaagct    540

tctgttgaag ttagacatac tcaatattat caacatgcta cagatattgc acgcactttg    600

aatattgata aatatgatat aattgcatgt gcttcaggtg atggtgtccc acatgaagtc    660

ttgaatggat tttatcaaag atctgataga gctgaagctt tcaataagat tacaataact    720

caattaccat gtggttcagg taatgcaatg agtgaatcat gtcatggtac aaataatcca    780

agttttgccg ctctatcatt attgaaatca agtacggtaa atttagattt aatggcttgt    840

acacaaggtg ataaaactta tgtttcattc ttaagtcaaa ctgtcggtgt tatagcagat    900

tctgatattg gtactgaagc acttagatgg ttaggtcctt caagatttga attaggtgtt    960

gcttataaag ttttatcaag atcaagatat ccatgtgata tatctgttaa atatgctgca   1020

aaatcgaaaa atgaattaag acaacatttt gatgaacatt ccactattgt ttcaacaaaa   1080

gatatccaaa taactgaaga tacttataat ttaaaatatg atccaaatgg tccaatacct   1140

gatgattggg aagagattga taaagatctt tcagaaaatt taggtatttt ctatacaggt   1200

aaaatgccat atattgcaaa agatgttcaa tttttccctg cagctttacc aaatgatggt   1260

acttttgatt tagttataac agatgctcgt acaagtatag cacgtatggc accaacttta   1320

ttatcattag atcaaggttc tcatgtttta caaccagaag ttcaacattc taaaataata   1380

gcatatagat taactccaaa gcagcaacat ggttatttaa gtgttgatgg tgaaagttat   1440

ccatttgaaa ctattcaagt tgaaattcta cccggtgctg caaagacttt actaagaaat   1500

ggtacttatg ttgaaacaaa tttttattga                                    1530
```